United States Patent [19]

Arch

[11] Patent Number: 4,880,834
[45] Date of Patent: Nov. 14, 1989

[54] METHOD FOR ADMINISTERING ETHANOLAMINE DERIVATIVES TO LIVESTOCK

[75] Inventor: Jonathan R. Arch, Banstead, England

[73] Assignee: Beecham Group p.l.c., England

[21] Appl. No.: 937,030

[22] PCT Filed: Mar. 3, 1986

[86] PCT No.: PCT/GB86/00114
§ 371 Date: Oct. 30, 1986
§ 102(e) Date: Oct. 30, 1986

[87] PCT Pub. No.: WO86/05075
PCT Pub. Date: Sep. 12, 1986

[30] Foreign Application Priority Data

Mar. 1, 1985 [GB] United Kingdom ............ 8505284
Aug. 22, 1985 [GB] United Kingdom ............ 8521068

[51] Int. Cl.$^4$ .............. A61K 31/195; A61K 31/235; A61K 31/195; A61K 31/16

[52] U.S. Cl. .................. 514/567; 514/533; 514/539; 514/562; 514/563; 514/564; 514/565; 514/597; 514/608; 514/629; 514/630; 514/651; 514/620; 514/653

[58] Field of Search .............. 514/562, 563, 564, 565, 514/566, 567, 533, 534, 539, 620, 597, 608, 629, 630

[56] References Cited

U.S. PATENT DOCUMENTS

| 4,146,638 | 3/1979 | Renth et al. .............. 514/534 |
| 4,404,222 | 9/1983 | Baker ....................... 514/534 |
| 4,654,371 | 3/1987 | Ainsworth et al. ........ 514/567 |

OTHER PUBLICATIONS

Blodinger–Formulation of Veterinary Dosage Forms, 1983, Marcel Deckker, Inc, New York and Basel, pp. 176–189.
The Merck Veterinary Manual, Fifth Edition, Merck & Co. Inc., Rahway, N.J., U.S.A., 1979, pp. 201, 202, 524 & 525.
Chemical Abstracts, vol. 94, 1981, 15371m.

Primary Examiner—Frederick E. Waddell
Attorney, Agent, or Firm—Jacobs & Jacobs

[57] ABSTRACT

A method for treating livestock to decrease birth mortality rate and to increase post-natal survival rate by administering ethanolamine derivatives is disclosed.

6 Claims, No Drawings

METHOD FOR ADMINISTERING ETHANOLAMINE DERIVATIVES TO LIVESTOCK

The present invention relates to the use of certain ethanolamine derivatives in a method for increasing weight gain and/or improving the feed utilisation efficiency and/or increasing the lean body mass and/or decreasing birth mortality rate and increasing post-natal survival rate; of livestock and the veterinary formulations comprising such compounds.

European Published Patent Application No. 0,006,735 discloses compounds of general formula (I):

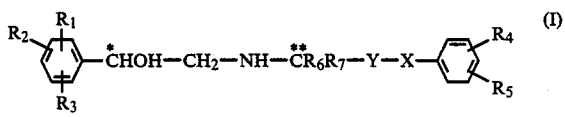

or a pharmaceutically acceptable salt thereof wherein $R^1$ is a hydrogen, fluorine or chlorine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino group; $R^2$ is a hydrogen, fluorine or chlorine atom or a hydroxyl group; $R^3$ is a hydrogen or chlorine atom or a hydroxyl group; $R^4$ is a carboxylic acid group or a salt, ester or amide thereof; $R^5$ is a hydrogen, chlorine or fluorine atom or a methyl, methoxyl or hydroxyl group or a carboxylic acid group or a salt, ester or amide thereof; $R^6$ is a hydrogen atom or a methyl, ethyl or propyl group; $R^7$ is a hydrogen atom or a methyl, ethyl or propyl group; X is an oxygen atom or a bond; and Y is an alkylene group of up to 6 carbon atoms or a bond; which compounds show anti-obesity and/or anti-hyperglycaemic activity.

European Patent Specification No. 0,023,385 discloses compounds of a general formula (II):

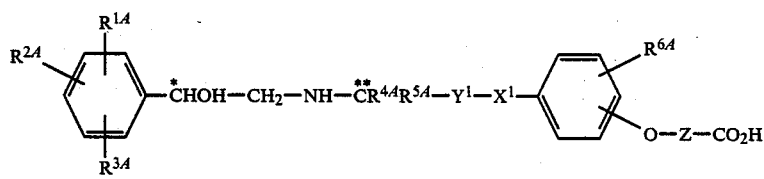

or a pharmaceutically acceptable salt, ester or amide thereof wherein $R^{1A}$ is a hydrogen, fluorine or chlorine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino group; $R^{2A}$ is a hydrogen, fluorine or chlorine atom or a hydroxyl group; $R^{3A}$ is a hydrogen or chlorine atom or a hydroxyl group; or $R^{1A}$, $R^{2A}$, and $R^{3A}$ each represents a bromine atom; $R^{4A}$ is a hydrogen atom or a methyl group; $R^{5A}$ is a hydrogen atom or a methyl group; $R^{6A}$ is a hydrogen, fluorine or chlorine atom or a methyl, methoxyl or hydroxy group; $X^1$ is an oxygen atom or a bond; $Y^1$ is an alkylene group of up to 6 carbon atoms or a bond; and Z is an alkylene, alkenylene or alkynylene group of up to 10 carbon atoms; which compounds show anti-obesity and/or anti-hyperglycaemic activity.

European patent specification No. 0,028,105 discloses a particular group of compounds, falling within formula (I), of formula (III):

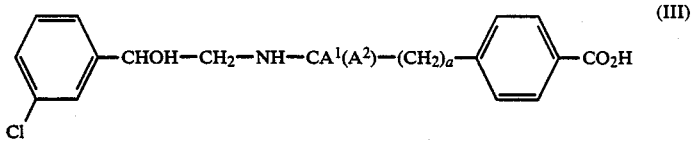

and esters, amides and pharmaceutically acceptable salts thereof wherein $A^1$ is a hydrogen atom or a methyl group and $A^2$ is a hydrogen atom or a methyl group and a is 1,2 or 3.

The compounds of formula (III) are described as having good anti-obesity and anti-glycaemic properties coupled with low side effects.

European patent specification No. 0,040,915 also discloses a particular group of compounds, falling within formula (I), of formula (IV)

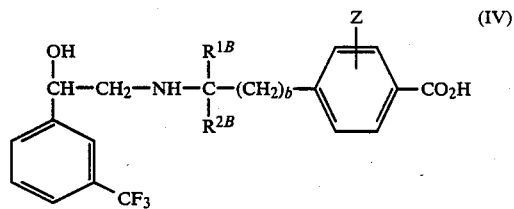

or a pharmaceutically acceptable salt, lower alkyl or aralkyl ester or amide thereof, wherein $R^{1B}$ and $R^{2B}$ which may be the same of different, are each a hydrogen atom or a methyl group, b is 1,2 or 3, and $Z^1$ is a $C_{1-6}$ alkyl or $C_{1-6}$ alkoxy group, or a halogen or hydrogen atom.

The compounds of formula (IV) are described as having anti-obesity and/or hypoglycaemic activity coupled with low cardiac stimulant activity. Particular compounds of formula (IV) also have anti-inflammatory activity.

European patent specification No. 0,040,000 discloses compounds of formula (V):

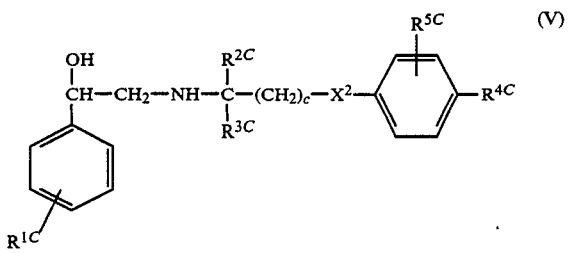

(V)

or a pharmaceutically acceptable salt thereof, in which $X^2$ is an oxygen atom or a bond, $R^{1C}$ is a hydrogen, fluorine, chlorine or bromine atom or a trifluoromethyl or $C_{1-4}$ alkyl group, each of $R^{2C}$ and $R^{3C}$ is a hydrogen atom or a $C_{1-4}$ alkyl group, $R^{4C}$ is a $C_{1-4}$ alkyl group, $R^{5C}$ is a hydrogen atom or a $C_{1-4}$ alkyl group and c is an integer of from 1 to 3.

The compounds of formula (V) are described as having anti-obesity and/or hypoglycaemic activity coupled with low cardiac stimulant activity. Derivatives of compound (V) are stated to have topical anti-inflammatory activity.

European Published Application No. 0,052,963 discloses compounds of formula (VI):

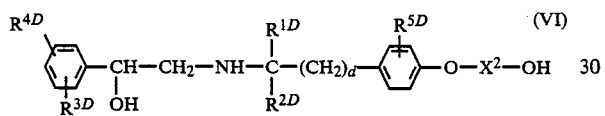

or a salt thereof; wherein $R^{1D}$ is hydrogen, methyl or ethyl; $R^{2D}$ is hydrogen, methyl or ethyl; $R^{3D}$ is hydrogen, fluorine, chlorine, bromine or trifluoromethyl; each of $R^{4D}$ and $R^{5D}$ is hydrogen, fluorine, chlorine, bromine, $C_{1-6}$ alkyl or $C_{1-6}$ alkoxy; d is 1 or 2; and $X^2$ is $C_{1-12}$ straight or branched alkylene.

The compounds of formula (VI) are described as having anti-obesity and/or hypoglycaemic and and/or anti-inflammatory and/or platelet aggregation inhibition activity coupled with low cardiac stimulant activity for particular compounds of formula (VI).

European patent specification No. 0,066,351 discloses compounds of formula (VII):

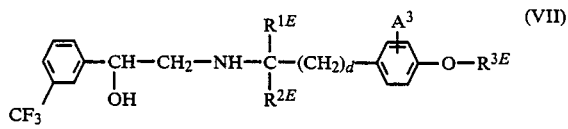

or a salt thereof; wherein
$R^{1E}$ is hydrogen or methyl;
$R^{2E}$ is hydrogen or methyl;
d' is 1 or 2;
$R^{3E}$ is hydrogen, $C_{1-12}$ alkyl, $C_{1-10}$ cycloalkyl or benzyl optionally substituted with $C_{1-6}$ alkyl, $C_{1-6}$ alkoxy, or halogen; and
$A^3$ is hydrogen, halogen, hydroxy, $C_{1-6}$ alkyl or $C_{1-6}$ alkoxy.

The compounds of formula (VII) are described as having anti-hyperglycaemic and/or anti-obesity and/or anti-inflammatory and/or platelet aggregation inhibition activity.

European patent specification No. 0,061,907 discloses compounds of formula (VIII):

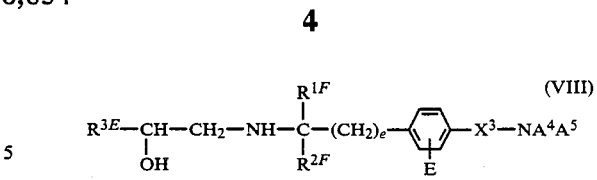

and salts thereof wherein
$R^{1F}$ is hydrogen or methyl;
$R^{2F}$ is hydrogen or methyl;
$R^{3F}$ is phenyl optionally substituted with one or two of the following: fluorine, chlorine, bromine, trifluoromethyl or $C_{1-6}$ alkyl, or is benzofuran-2-yl;
e is 1 or 2;
$X^3$ is a $C_{1-15}$ straight or branched alkylene group;
$A^4$ is hydrogen, $C_{1-6}$ alkyl, or optionally substituted benzyl;
$A^5$ is hydrogen, $C_{1-6}$ alkyl, or optionally substituted benzyl; and
E is hydrogen, halogen, $C_{1-6}$ alkoxy, $C_{1-6}$ alkyl, or mono- or di-$C_{1-6}$ alkylamino.

The compounds of formula (VIII) are described as having anti-obesity and/or anti hypoglycaemic and/or anti-inflammatory and/or platelet aggregation inhibition activity, coupled with low cardiac stimulant activity for certain compounds of formula (VIII).

European Published Patent Application No. 0,070,133 discloses compounds of formula (IX):

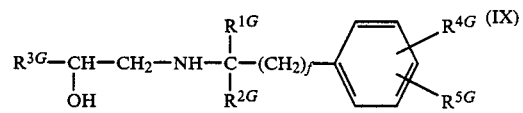

and salts and in vivo hydrolysable acyl derivatives thereof, wherein
$R^{1G}$ is hydrogen or methyl;
$R^{2G}$ is hydrogen or methyl;
$R^{3G}$ is phenyl unsubstituted or substituted with one or two of the following:- fluorine, chlorine, bromine, trifluoromethyl, $C_{1-6}$ straight or branched chain alkyl or $C_{1-6}$ straight or branched chain alkoxy; or is benzofuran-2-yl;
$R^{5G}$ is a hydrogen, halogen, hydroxy, lower alkyl or lower alkoxy;
$R^{4G}$ is a moiety

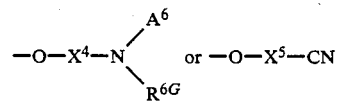

wherein
$X^4$ is a $C_{2-10}$ alkylene group which may be straight or branched, provided that the oxygen and nitrogen are separated by at least two carbon atoms,
$X^5$ is a $C_{1-9}$ alkylene group which may be straight or branched,
$A^6$ is hydrogen; a $C_{1-6}$ straight or branched alkyl group or benzyl optionally substituted with halogen, lower alkyl or lower alkoxy,
$R^{6G}$ is hydrogen; a $C_{1-6}$ straight or branched alkyl group; a $C_{1-6}$ straight or branched alkylsulphonyl group or

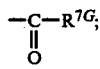

$R^{7G}$ is a $C_{1-6}$ straight or branched alkyl group; $C_{1-6}$ straight or branched alkoxy; amino, mono- or di-($C_{1-6}$ straight or branched chain alkyl)amino; or

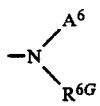

is a 5,6 or 7 membered cyclic amino group optionally containing a second hetero atom selected from oxygen, nitrogen and sulphur, and f is 1 or 2.

The compounds of formula (IX) are described as having anti-obesity and/or anti-hyperglycaemic and/or anti-inflammatory and/or platelet aggregation inhibition activity, coupled with low cardiac stimulant activity for particular compounds of formula (IX).

Kingdom patent specification No. 1,574,208 disclose compounds of formula (X):

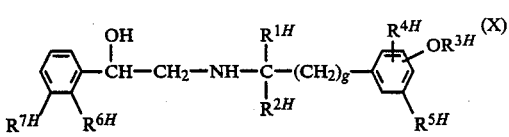

or a salt thereof;
wherein
$R^{1H}$ is hydrogen or methyl,
$R^{2H}$ is hydrogen or methyl,
$R^{3H}$ is hydrogen, $C_{1-12}$ straight or branched alkyl, $C_{3-10}$ cycloalkyl, phenyl ($C_{1-4}$)alkyl or benzyl optionally substituted by $C_{1-4}$ alkyl, $C_{1-4}$ alkoxy or halogen;
$R^{4H}$ is hydrogen, halogen, hydroxy, $C_{1-4}$ alkyl or $C_{1-4}$ alkoxy,
$R^{5H}$ is hydrogen or fluorine,
$R^{6H}$ is hydrogen or fluorine,
$R^{7H}$ is halogen; and
g is 1 or 2

The compounds of formula (X) have anti-hyperglycaemic and anti-obesity activity.

European Patent Specification No. 0,095,827 discloses compounds of formula (XI):

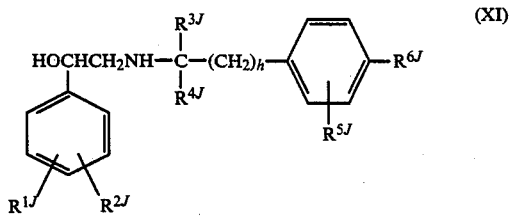

or a salt thereof,
wherein
$R^{1J}$ is hydrogen, halogen or trifluoromethyl,
$R^{2J}$ is hydrogen or halogen,
$R^{3J}$ is hydrogen or methyl,
$R^{4J}$ is hydrogen or methyl,
$R^{5J}$ is hydrogen or halogen,
$R^6$ is

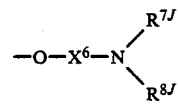

$X^6$ is a $C_{3-20}$ straight or branched alkylene group having at least two carbon atoms interposed between the oxygen and nitrogen atoms and having a hydroxyl substituent on a carbon atom not directly bonded to the oxygen or nitrogen atoms; $R^{7J}$ is hydrogen, a $C_{1-6}$ straight or branched chain alkyl group, or optionally substituted benzyl, $R^{8J}$ is hydrogen, a $C_{1-6}$ straight or branched chain alkyl group, or optionally substituted benzyl, or

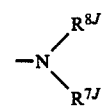

is a 5,6 or 7 membered, saturated heterocyclic group containing a total of one or two heteroatoms, the second hetero-atom, when present, being selected from nitrogen, oxygen and sulphur, and h is 1 or 2.

The compounds of formula (XI) are described as having anti-hyperglycaemic and/or anti-obesity activity, coupled with low cardiac stimulant activity for particular compounds of formula (XI).

European Patent Application No. 0,099,707 discloses compounds of formula (XII):

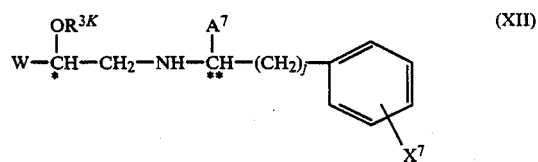

or a pharmaceutically acceptable salt, ester or amide thereof, in which:

W is an optionally substituted phenyl group of the formula:

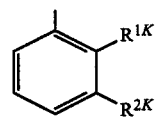

wherein
$R^{1K}$ is hydrogen or fluorine,
$R^{2K}$ is hydrogen, $C_{1-6}$ alkyl, halogen or trifluoromethyl; or
W is a phenoxymethyl or benzofuran-2-yl group;
$R^{3K}$ is $C_{1-12}$ alkyl or phenyl-($C_{1-6}$)-alkyl;
$A^7$ is hydrogen or methyl,
$X^7$ is carboxy, $-Z^2-CO_2H$, $-Z^2-OH$, $T-Z^2-CO_2H$, $-Z^2-NR^{4K}R^{5K}$, $-T-Y^2-OM$, $-T-Y^2-NR^{4K}R^{5K}$, or $-T-R^{6K}$, in the para- or meta-position with respect to the $-(CH_2)_j$ group, wherein
$R^{4K}$ and $R^{5K}$ are each hydrogen or $C_{1-6}$ alkyl,
$R^{6K}$ is $C_{1-6}$ alkyl,
T is O, S, $-NH$ or $-N-R^{7K}$, in which $R^{7K}$ is $C_{1-6}$ alkyl, $Z^2$ is a $C_{1-10}$ straight or branched alkylene group optionally containing a carbon-carbon double bond; $Y^2$ is a $C_{2-10}$ straight or branched alkylene group, provided that the hetero atoms in $-T-Y^2-OM$ and $-T-Y^2NR^{4K}R^{5K}$ are separated by at least two carbon atoms, M is hydrogen, $C_{1-6}$ alkyl or phenyl and j is 1 or 2.

The compounds of formula (XII) are disclosed as having anti-hyperglycaemic and/or anti-obesity and/or anti-inflammatory and/or platelet aggregation inhibition activity coupled with low cardiac stimulant activity.

European Published Patent Application No. 0,139,921 discloses compounds of formula (XIII):

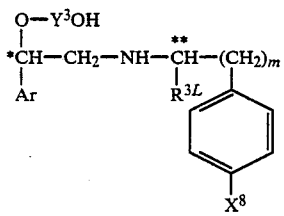
(XIII)

or a pharmaceutically acceptable salt, ester or amide thereof, wherein: Ar is benzofuran-2-yl, or phenyl optionally substituted by groups $R^{1L}$ and/or $R^{2L}$ wherein $R^{1L}$ is halogen, trifluoromethyl or hydroxy and $R^{2L}$ is halogen; $R^{3L}$ is hydrogen or methyl; and $X^8$ is $-O(CH_2)_kCO_2H$, $-O(CH_2)_lM^1$ or $-CO_2H$ in which k is an integer from 1 to 6, l is an integer from 2 to 7, $M^1$ is hydroxy, $C_{1-6}$ alkoxy, phenyl $C_{1-6}$ alkoxy, or $-NR^{4L}R^{5L}$ in which $R^{4L}$ and $R^{5L}$ are each hydrogen or $C_{1-6}$ alkyl or together form a five or six membered heterocyclic ring;

$Y^3$ is $C_{2-6}$ straight or branched alkylene, with at least two carbon atoms between the $-O-$ and $-OH$; and m is 1 or 2.

The compounds of formula (XIII) are described as having anti-obesity and/or anti-hyperglycaemic activity.

European Published Patent Application No. 0,142,102 discloses compounds of formula (XIV):

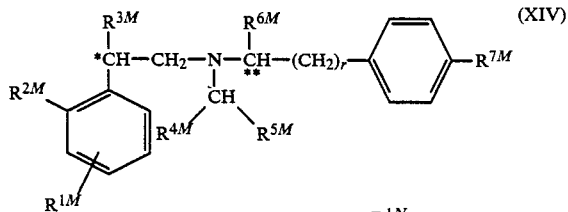
(XIV)

or a pharmaceutically acceptable salt thereof, in which
$R^{1M}$ is hydrogen, halogen or trifluoromethyl;
$R^{2M}$ is hydrogen or halogen;
$R^{3M}$ is hydroxyl, $C_{1-6}$ alkoxy or

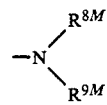

where
$R^{8M}$ and $R^{9M}$ are each hydrogen or $C_{1-6}$ alkyl; $R^{4M}$ is hydrogen or $C_{1-6}$ alkyl, $R^{5M}$ is hydrogen, $C_{1-6}$ alkyl, $C_{1-6}$ alkyl optionally substituted by hydroxy; cyano, $C_{1-6}$ alkenyl or $C_{1-6}$ alkynyl optionally substituted by carboxy or esters and amides thereof, phenyl, $C_{1-6}$ alkyl phenyl or a group

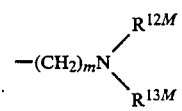

wherein $R^{12M}$ and $R^{13M}$ are each hydrogen or $C_{1-6}$ alkyl or together, along with the nitrogen to which they are attached, form a 5- or 6- membered ring, and n is 1 or 2; $R^{6M}$ is hydrogen or methyl: $R^{7M}$ is $-O(CH_2)_pCO_2H$, $-O(CH_2)_qM^2$, $-CO_2H$; or an ester or amide thereof in which p is an integer from 1 to 6 q is an integer from 2 to 7, and $M^2$ is hydroxy, $C_{1-6}$ alkoxy or

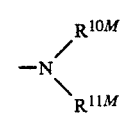

in which
$R^{10M}$ and $R^{11M}$ are each hydrogen or $C_{1-6}$ alkyl or

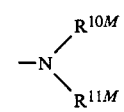

together form a five or six membered ring; and r is 1 or 2; with the proviso that when n is 2 and $R^{1M}$, $R^{2M}$, $R^{4M}$ and $R^{6M}$ are each hydrogen and $R^{3M}$ is hydroxyl, $R^{5M}$ is not hydroxymethyl or 1-hydroxy ethyl when $R^{7M}$ is $CONH_2$.

The compounds of EP142102A are described as having anti-hyperglycaemic and/or anti-obesity activity.

European Pat. No. 0,025,331 discloses compounds of formula (XV):

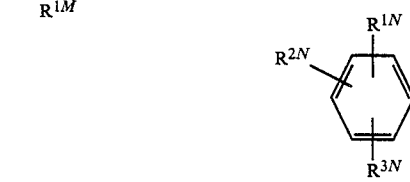—CHOH—$CH_2$—NH—$C(R^{5N})R^{6N}$—$Y^4$—$X^9$—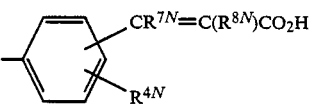

(XV)

or a pharmaceutically acceptable ester, amide or salt thereof wherein $R^{1N}$ is a hydrogen, fluorine or chlorine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino, $R^{2N}$ is a hydrogen, fluorine or chlorine atom or a hydroxyl group; $R^{3N}$ a hydrogen or chlorine atom or a hydroxyl group; or $R^{1N}$, $R^{2N}$ and $R^{3N}$ each independently represents a bromine atom; $R^{4N}$ is a hydrogen, chlorine or fluorine atom or a methyl, methoxyl or hydroxy group or a carboxylic acid group or a salt, ester or amide thereof; $R^{5N}$ is a hydrogen atom or a methyl group; $R^{6N}$ is a hydrogen atom or a methyl group; $R^{7N}$ is a hydrogen atom or a methyl or ethyl group; $R^{8N}$ is a hydrogen atom or a methyl or ethyl group; $X^9$ is an oxygen atom or a bond; and $Y^4$ is an alkylene group of up to 5 carbon atoms or a bond.

The compounds of EP25331 are described as being useful for the treatment of obesity or hyperglycaemia.

European Published Application No. 0,089,154 discloses inter alia compounds of formula (XVI):

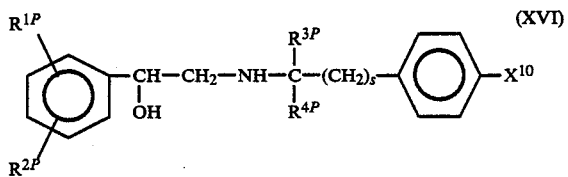
(XVI)

or a pharmaceutically acceptable salt thereof, wherein;
$R^{1P}$ is hydrogen, halogen or trifluoromethyl,
$R^{2P}$ is hydrogen or halogen,
$R^{3P}$ is hydrogen or methyl,
$R^{4P}$ is hydrogen or methyl,
s is 1,
$X^{10}$ is $-Y^5-SR^{5P}$,

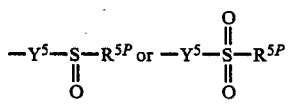

$R^{5P}$ is optionally substituted benzyl or $C_{1-12}$ straight or branched alkyl optionally substituted by carboxy, $C_{1-6}$ alkoxycarbonyl, benzyloxycarbonyl, aminocarbonyl, mono- or di-($C_{1-6}$)alkylamino-carbonyl, hydroxy, $C_{1-6}$ alkoxy, benzyloxy, phenoxy, amino, mono- or di-($C_{1-6}$)alkylamino, $C_{1-6}$ alkylthio, benzylthio, or phenylthio
provided that, when $R^{5P}$ is alkyl substituted by hydroxy, alkoxy, alkylthio, phenylthio, benzylthio, amino, alkylamino or benzyloxy, such substituents are separated from the sulphur atom by at least two carbon atoms, and $Y^5$ is methylene or a bond.

The compounds of EP89154A are described as having anti-obesity and/or anti-hyperglycaemic and/or anti-inflammatory activity, this activity being coupled with low cardiac stimulant activity for particular members of the class.

European Published Patent Application No. 0,091,749 discloses compounds of formula (XVII):

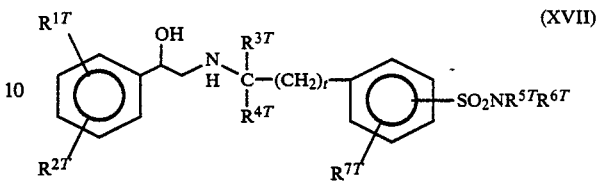
(XVII)

or a salt thereof, wherein;
$R^{1T}$ is hydrogen, halogen or trifluoromethyl,
$R^{2T}$ is hydrogen or halogen,
$R^{3T}$ is hydrogen or methyl,
$R^{4T}$ is hydrogen or methyl,
$R^{5T}$ is hydrogen, $C_{1-10}$ straight or branched alkyl or optionally substituted benzyl,
$R^{6T}$ is hydrogen, $C_{1-10}$ straight or branched alkyl, or optionally substituted benzyl, or $R^{5T}$ and $R^{6T}$ taken together with the attached nitrogen atom represent a heterocylic ring,
$R^{7T}$ is hydrogen or halogen, and t is 1.

The compounds of EP91749A are described as having anti-obesity and/or anti-hyperglycaemic activity coupled with low cardiac stimulant activity.

European patent specification No. 0,029,320 discloses compounds of formula (XVIII):

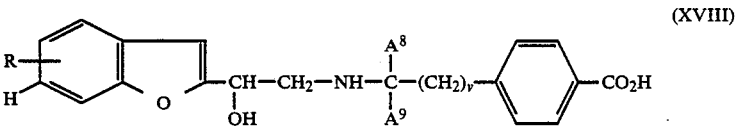
(XVIII)

or a lower alkyl ester, an amide, comprising an amino, mono- or di-($C_{1-6}$) alkyl amino moiety or pharmaceutically acceptable salts thereof, wherein $A^8$ is hydrogen or methyl; $A^9$ is hydrogen or methyl; v is 1,2 or 3; and R is hydrogen, chlorine, bromine, hydroxy, methoxy, nitro, amino or trifluoromethyl.

The compounds of EP29320 are described as having good anti-obesity and/or anti-hyperglycaemic activity coupled with a low level of side effects.

European Published Patent Application No. 0,051,917 discloses compounds of formula (XIX):

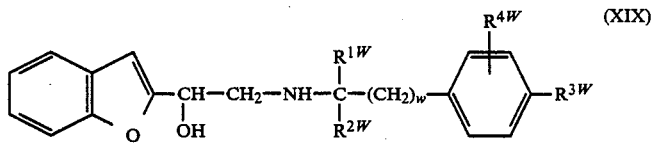
(XIX)

or an ester, amide or salt thereof, where appropiate, wherein
$R^{1W}$ is hydrogen or methyl;
$R^{2W}$ is hydrogen or methyl;
$R^{3W}$ is hydrogen, hydroxy, ($C_{1-6}$) alkoxy, benzyloxy or a group $X^{10}-Y^6-Z^3$, wherein
(i) $X^{11}$ is a bond or oxygen, $Y^6$ is $C_{1-6}$ straight or branched alkylene, and $Z^3$ is hydrogen or carboxy; or
(ii) $X^{11}$ is a bond or moiety $-O-CH_2-$, $Y^6$ is $C_{2-6}$ straight or branched alkenylene and $Z^3$ is carboxy;

$R^{4W}$ is selected from hydrogen, hydroxy, halogen, $C_{1-6}$ alkyl and $C_{1-6}$ alkoxy; and w is 1,2 or 3.

The compounds of EP51917A are described as having anti-obesity, hypoglycaemic, anti-inflammatory and platelet-aggregation inhibition activity.

European Published Patent Application No. 0,140,359 discloses compounds of formula (XX):

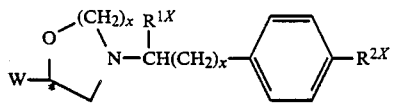
(XX)

or a salt thereof, in which
W is phenyl optionally substituted by halogen or trifluoromethyl, or a benzofuran-2-yl group,
$R^{1X}$ is hydrogen or methyl,
$R^{2X}$ is carboxyl or a group $O-Z^4-CO_2H$ or an ester or amide thereof; a group $O-E^1-NR^{3X}R^{4X}$ or a group $O-E^1-OR^{5X}$, wherein
$R^{3X}$, $R^{4X}$ and $R^{5X}$ each represents hydrogen or $C_{1-6}$ alkyl, $Z^4$ is a $C_{1-6}$ straight or branched alkylene chain, x is 1 or 2, y is 2 or 3, and $E^1$ is $C_{2-7}$ straight or branched alkylene chain with at least two carbon atoms separating the two heteroatoms in the group $R^{2X}$.

The compounds of EP140359A are described as having anti-hyperglycaemic and/or anti-obesity activity.

European Published Patent Application No. 0,063,004 discloses compounds of formula (XXI):

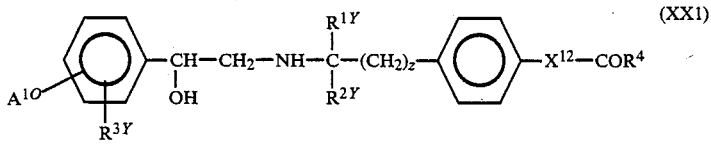
(XXI)

and salts thereof;
wherein
$R^{1Y}$ is hydrogen or methyl;
$R^{2Y}$ is hydrogen or methyl;
$R^{3Y}$ is hydrogen, fluorine, chlorine, bromine, trifluoromethyl or $C_{1-6}$ alkyl;
z is 1 or 2;
$X^{12}$ is $C_{1-6}$ straight or branched alkylene;
$R^{4Y}$ is $C_{1-6}$ alkoxy, hydroxy or amino optionally substituted with one or more lower alkyl groups; and
$A^{10}$ is hydrogen, fluorine, chlorine or bromine.

The compounds of EP63004A are described as having anti-obesity and/or anti-hyperglycaemic activity.

European Published Patent Application No. 0,170,135 discloses compounds of formula (XXII):

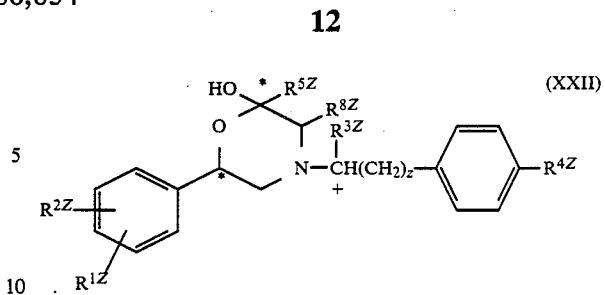
(XXII)

or a pharmaceutically acceptable salt thereof, in which
$R^{1Z}$ is hydrogen, halogen, or trifluoromethyl;
$R^{2Z}$ is hydrogen or halogen;
$R^{3Z}$ is hydrogen or methyl;
$R^{4Z}$ is $-O(CH_2)_\delta CO_2H$ or an ester or amide derivative thereof, $O(CH_2)_\epsilon M^4$ or $-CO_2H$ or an ester or amide derivative thereof wherein
$\delta$ is an integer from 1 to 6,
$\epsilon$ is an integer from 2 to 7, and
$M^4$ is hydroxy, $C_{1-6}$ alkoxy or

wherein
$R^{6Z}$ and $R^{7Z}$ are each hydrogen or $C_{1-6}$ alkyl or

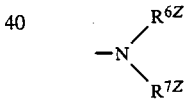

together form a five or six membered ring;
$R^{5Z}$ is $C_{1-6}$ alkyl; $C_{1-6}$ alkyl substituted by carboxy or esters and amides thereof; or phenyl optionally substituted by $C_{1-6}$ alkyl, halogen, alkoxy or trifluoromethyl;
$R^{8Z}$ is hydrogen or $C_{1-6}$ alkyl or $R^{8Z}$ together with $R^{5Z}$ form a carbocyclic ring; and $\alpha$ is 1 or 2.

The compounds of formula (XXII) are described as having anti-hyperglycaemic and/or anti-obesity activity. European patent specification No. 0,021,636 discloses compounds of formula (XXIII):

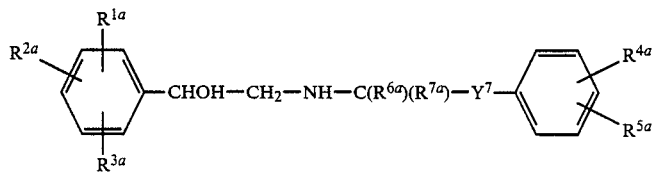
(XXIII)

or a pharmaceutically acceptable salt thereof, wherein
$R^{1a}$ is a hydrogen, fluorine, or chlorine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino; $R^{2a}$ is a hydrogen, fluorine or chlorine atom or a hydroxyl group; $R^{3a}$ is a hydrogen or chlorine atom or a hydroxyl group; or $R^{1a}$, $R^{2a}$ and $R^{3a}$ each independently represents a bromine atom; $R^{4a}$ is an alkyl group of 1 to 10 carbon atoms substituted by a hydroxyl, lower alkoxyl or OCH$_2$CO$_2$H group or lower alkyl ester thereof; $R^{5a}$ is a hydrogen, chlorine or fluorine atom or a methyl, methoxyl or hydroxyl group or a carboxylic acid group or a salt, ester or amide thereof; $R^{6a}$ is a hydrogen atom or a methyl, ethyl or propyl group; $R^{7a}$ is a hydrogen atom or a methyl, ethyl or propyl group; and $Y^7$ is an alkylene group of up to 6 carbon atoms or a bond.

European Published Application No. 0,102,213 discloses compounds of formula (XXIV):

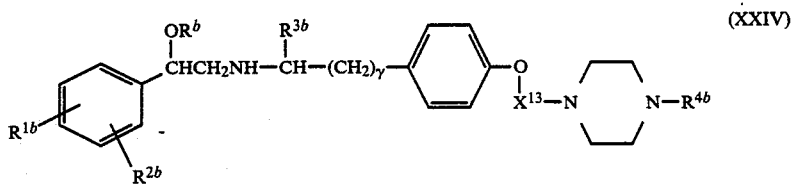

or a salt thereof,
wherein
$R^b$ is hydrogen or $C_{1-6}$ alkyl,
$R^{1b}$ is hydrogen, or fluorine,
$R^{2b}$ is hydrogen, halogen or trifluoromethyl,
$R^{3b}$ is hydrogen or methyl,
$R^{4b}$ is hydrogen, $C_{1-6}$ alkyl, optionally substituted benzyl, or optionally substituted phenyl $X^{13}$ is $C_{2-10}$ straight or branched alkylene having at least two carbon atoms interposed between the oxygen and nitrogen atoms and
$\gamma$ is 1 or 2.

The compounds of EP102213A are described as having anti-obesity and/or anti-hyperglycaemic activity coupled with low cardiac stimulent activity.

It has now surprisingly been discovered that these compounds may be used to increase weight gain and/or improve the feed utilisation efficiency and/or increase the lean body mass and/or decrease birth mortality rate and increase the post-natal survival rate; of livestock.

Accordingly, the present invention provides a method for increasing the weight gain and/or improving the feed utilisation efficiency and/or increasing the lean body mass and/or decreasing birth mortality rate and increasing post-natal survival rate; of livestock, which method comprises the administration to livestock of an effective, non-toxic amount of a compound selected from the list consisting of compounds of the, hereinbefore defined, formulae: (I), (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII) and (XXIV); or, where appropriate, a veterinarily acceptable salt, ester or amide thereof.

Suitably, the invention provides a method for increasing the weight gain and/or improving the feed utilisation efficiency and/or increasing the lean body mass of livestock.

Suitably, the invention provides a method for decreasing birth mortality rate and increasing the post-natal survival rate of livestock.

Suitable livestock include poultry (especially turkeys and chickens), cattle, pigs, sheep or goats.

Suitably, the invention provides a method for increasing the weight gain and/or improving the feed utilisation efficiency and/or increasing the lean body mass of poultry (especially turkeys and chickens), cattle, pigs or sheep.

It will be understood that the advantages provided by the present invention relating to the decrease in birth mortality rate and increase in post-natal survival rate are provided by administration to female parent livestock or the newly-born livestock, the decrease in birth mortality rate and increase in post-natal survival rate relating primarily to the newly born livestock.

In a particular aspect, the present invention provides a method for decreasing birth mortality rate and increasing post-natal survival rate of livestock, which method comprises the administration to pregnant livestock of an effective, non-toxic amount of a compound selected from the list consisting of compounds of the, hereinbefore defined, formulae: (I), (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII), and (XXIV); or, where appropriate, a veterinarily acceptable salt, ester or amide thereof;

Suitable pregnant livestock include pregnant cows, sows and ewes.

The method of the invention is particularly suitable for decreasing the birth mortality rate and increasing the post-natal survival rate of lambs by administration to pregnant ewes.

The present invention also encompasses the use of a compound selected from a list consisting of compounds of the, hereinbefore defined, formulae: (I), (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII) and (XXIV); or where appropriate a veterinarily acceptable salt, ester or amide thereof for the manufacture of a veterinarily acceptable formulation for decreasing the birth mortality rate and increasing the post-natal survival rate of livestock.

Suitably, the invention comprises the administration of a compound of formula (I) or a veterinarily acceptable salt, ester or amide thereof.

Suitably, the invention comprises the administration of a compound of formula (II) or a veterinarily acceptable salt, ester or amide thereof.

Suitably, the invention comprises the administration of a compound of formula (III) or a veterinarily acceptable salt, ester or amide thereof.

Suitably, the invention comprises the administration of a compound of formula (IV) or a veterinarily acceptable salt, ester or amide thereof.

Suitably, the invention comprises the administration of a compound of formula (V) or a veterinarily acceptable salt thereof.

Suitably, the invention comprises the administration of a compound of formula (VI) or a veterinarily acceptable salt thereof.

Suitably, the invention comprises the administration of a compound of formula (VII) or a veterinarily acceptable salt thereof.

Suitably, the invention comprises the administration of a compound of formula (VIII) or a veterinarily acceptable salt thereof.

Suitably, the invention comprises the administration of a compound of formula (IX) or a veterinarily acceptable salt or in-vivo hydrolysable acyl derivative thereof.

Suitably, the invention comprises the administration of a compound of formula (X) or a veterinarily acceptable salt thereof.

Suitably, the invention comprises the administration of a compound of formula (XI) or a veterinarily acceptable salt thereof.

Suitably, the invention comprises the administration of a compound of formula (XII) or a veterinarily acceptable salt, ester or amide thereof.

Suitably, the invention comprises the administration of a compound of formula (XIII) or a veterinarily acceptable salt, ester or amide thereof.

Suitably, the invention comprises the administration of a compound of formula (XIV) or a veterinarily acceptable salt, ester or amide thereof.

Suitably, the invention comprises the administration of a compound of formula (XV) or a veterinarily acceptable salt, ester or amide thereof.

Suitably, the invention comprises the administration of a compound of formula (XVI) or a veterinarily acceptable salt thereof.

Suitably, the invention comprises the administration of a compound of formula (XVII) or a veterinarily acceptable salt thereof.

Suitably, the invention comprises the administration of a compound of formula (XVIII) or a veterinarily acceptable salt, ester or amide thereof.

Suitably, the invention comprises the administration of a compound of formula (XIX) or a veterinarily acceptable salt, ester or amide thereof.

Suitably, the invention comprises the administration of a compound of formula (XX) or a veterinarily acceptable salt, ester or amide thereof.

Suitably, the invention comprises the administration of a compound of formula (XXI) or a veterinarily acceptable salt thereof.

Suitably, the invention comprises the administration of a compound of formula (XXII) or a veterinarily acceptable salt, ester or amide thereof.

Suitably, the invention comprises the administration of a compound of formula (XXIII) or a veterinarily acceptable salt, ester or amide thereof.

Suitably, the invention comprises the administration of a compound of formula (XXIV) or a veterinarily acceptable salt thereof.

Preferably, the invention comprises the administration of a compound of formula (I) or (II) or a veterinarily acceptable salt, ester or amide thereof;

When the invention comprises the administration of a compound of formula (I) as herein before defined:

Apt values for $R^1$ include the hydrogen, fluorine and chlorine atoms and the hydroxymethyl, hydroxyl, methoxyl, acetamido, amino, methylsulphonylmethyl, methylsulphonamido, trifluoromethyl, ureido or p-methoxybenzylamino group.

Particularly suitable values for $R^2$ are the hydrogen and chlorine atoms. Aptly $R^3$ is a hydrogen, hydroxyl or chlorine.

Particularly suitable groups $R^1R^2R^3C_6H_2$ include the phenyl; 3-ureido-4-hydroxyphenyl; 3-methane sulphonylamido-4-hydroxyphenyl; 3,5-dihydroxyphenyl; 3,4-dihydroxy-phenyl; 3-methylsulphonylmethyl-4-hydroxyphenyl; 3,5-dichloro-4-aminophenyl; 2-chlorophenyl; 2-methoxy-3,4-dihydroxyphenyl; 3-hydroxymethyl-4-hydroxyphenyl; 3-trifluoromethylphenyl; and 3-(p-methoxybenzyl)amino-4-hydroxyphenyl groups.

A preferred group $R^1R^2R^3C_6H_2$ is the phenyl group.

Another preferred group $R^1R^2R^3C_6H_2$ is the 3,5-dichloro-4-aminophenyl group. A further preferred group $R^1R^2R^3C_6H_2$ is the 3-hydroxy-methyl-4-hydroxyphenyl group. A further preferred group $R^1R^2R^3C_6H_2$ is the 3-trifluoromethylphenyl group. Apt groups of the formula $R^4$ include those of the sub-formulae (a)-(e):

$$—CO_2H \qquad (a)$$

$$—CO_2{}^-1/qA^{q+} \qquad (b)$$

$$—CO_2R_8 \qquad (c)$$

$$—CO.NH_2 \qquad (d)$$

$$—CO.NR_9R_{10} \qquad (e)$$

wherein $A^{q+}$ is an ion wherein q is aptly 1 or 2; $R^8$ is a group such that $CO_2R^8$ is an ester group; and $R^9$ is a lower alkyl group and $R_{10}$ is a hydrogen atom or a lower alkyl group or is joined to $R^9$ to form a saturated 5, 6 or 7 membered ring.

When used herein the term "lower" means that the group contains not more than 6 carbon atoms, preferably not more than 4.

Particularly apt values for $R^4$ include those of the sub-formulae (a), (b) or (c).

An especially favoured value for $R^4$ is that of the sub-formula (c). In such compounds it is suitable that the moiety $R^8$ is such that the ester group is hydrolysed in-vivo to yield the corresponding compound wherein $R^4$ is a group of the sub-formula (a) or a salt thereof.

Particularly suitable values for $R^8$ include lower alkyl groups, lower alkyl groups substituted by a hydroxyl group not on the α-carbon atom and groups of the sub-formulae (f) or (g):

$$—CHR_{11}—O—CO—R_{12} \qquad (f)$$

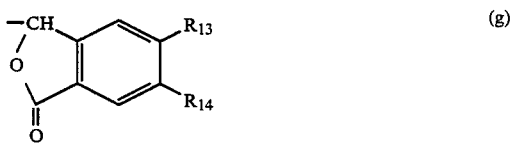

wherein $R^{11}$ is a hydrogen atom or a methyl group; $R^{12}$ is a lower alkyl or phenyl group; $R^{13}$ is a hydrogen atom or a methyl or methoxyl group; and $R^{14}$ is a hydrogen atom or a methyl or methoxyl group.

Certain particularly suitable values for $R^8$ include the methyl, ethyl, propyl and butyl groups, for example the methyl group and the isopropyl group.

Preferably $R^8$ is a methyl group.

The point of attachment of the group $R^4$ is aptly meta-or para- to the point of attachment of the phenyl group to the rest of the molecule.

Suitably $R^5$ is hydrogen or methoxyl.

Preferably $R^5$ is hydrogen.

A favourable value for $R^6$ is a hydrogen atom. A further favourable value for $R^6$ is the methyl group. A favourable value for $R^7$ is the hydrogen atom. A further favourable value for $R^7$ is the methyl group. Most favourably $C(R^6)R^7$ is a $CH_2$, $CH(CH_3)$, or $C(CH_3)_2$ group, preferably $CH(CH_3)$.

Suitably, when the method of the invention comprises the administration of a compound of formula (II), as hereinbefore defined, or a veterinarily acceptable salt, ester or amide thereof the $O-Z-CO_2H$ moiety or the said salt, ester or amide thereof, is attached para- to the $-X^1-$ moiety.

Suitable values for $R^{14}$ include the hydrogen, fluorine, chlorine and bromine atoms and the trifluoromethyl, hydroxymethyl, hydroxyl and amino groups.

Suitably $X^1$ in the compounds of the formula (II) is a bond.

Preferred groups $Y^1$ are of the formula $-(CH_2)_{n'}-$ where n' is an integer from 1 to 5, particularly 1 or 2.

Particularly suitable values for each of $R^{24}$ and $R^{34}$ are the hydrogen and chlorine atoms.

Particularly suitable groups $R^{14}R^{24}R^{34}C_6H_2$ include the phenyl; 2-fluorophenyl; 3-trifluoromethylphenyl; 3-chlorophenyl, 3,5-dichloro-4-aminophenyl; 2-chlorophenyl; 3-hydroxymethyl-4-hydroxyphenyl; 3-chlorophenyl; and 3,5-dichloro-4-amino groups, preferably 3-chlorophenyl.

In accordance with conventional usage, the terms "alkenylene" and "alkynylene" do not extend to systems containing an oxygen atom attached to the carbon of a carbon-carbon double bond.

The group Z may be branched, for example to carry one or two methyl groups, but it is more suitably unbranched. Aptly the group Z contains 1 to 6 carbon atoms and more suitably 1 to 4 carbon atoms.

Groups Z include $CH_2$, $CH_2CH_2$, $CH_2CH_2CH_2$, $CH_2CH_2CH_2CH_2$, $CH_2CH=CH$.

A particularly favoured group Z is the $CH_2$ group.

Favourably, the invention comprises the administration of an ester of the compound of formula (II) including those esters that are hydrolysed in-vivo to yield the corresponding compound of formula (II) per se or its salt.

Particularly suitable in-vivo hydrolysable ester forming groups include lower alkyl groups, lower alkyl groups substituted by a hydroxyl group not on the α-carbon atom and groups of the sub-formulae (f) and (g) as hereinbefore defined.

In a preferred aspect the method of the invention comprises the administration of a preferred sub-group of the compounds of formula (I), being compounds of formula (IIIA):

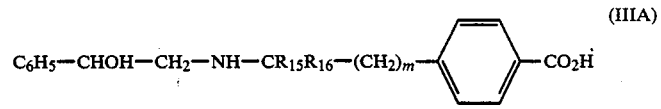

or a veterinarily acceptable salt, ester or amide thereof, wherein $R^{15}$ is a hydrogen atom or a methyl group; $R^{16}$ is a hydrogen atom or a methyl group; and m' is 1,2 or 3.

Most suitably, $R^{15}$ is a hydrogen atom.

Most suitably $R^{16}$ is a methyl group.

Preferably m' is 1.

Esters of the compound of the formula (IIIA) include those of the sub-formulae (c), (f) and (g) as defined in relation to formula (I).

A particularly preferred ester of the compound of formula (IIIA) is the methyl ester.

In a second preferred aspect the invention comprises the administration of another preferred sub-group of the compounds of formula (I), being compounds of formula (IVA):

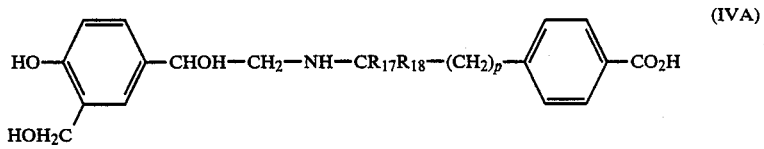

or a veterinarily acceptable salt, ester or amide thereof wherein $R^{17}$ is a hydrogen atom or a methyl group; $R^{18}$ is a hydrogen atom or a methyl group; and p' is 1, 2 or 3.

Most suitably $R^{17}$ is a hydrogen atom. Most suitably $R^{18}$ is a methyl group.

Preferably p' is 1.

Esters of the compounds of the formula (IVA) include those of the sub-formulae (c), (f) and (g) as defined in relation to formula (I).

A particularly preferred ester of the compound of formula (IVA) is the methyl ester.

In a further preferred aspect, the invention comprises the administration of a preferred sub-group of the compounds of formula (II), being compounds of formula (VA):

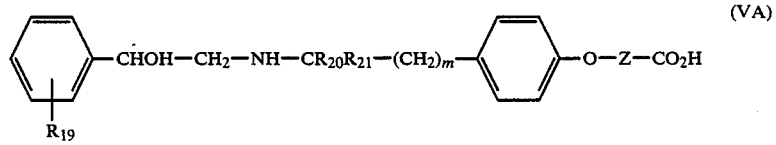

or a veterinarily acceptable salt, ester or amide thereof, wherein $R^{19}$ is a hydrogen, fluorine or chlorine atom or a trifluoromethyl group, Z is as defined in relation to formula (II), $R^{20}$ is a hydrogen atom or a methyl group; $R^{21}$ is a hydrogen atom or a methyl group; and m" is 1, 2 or 3.

Preferably Z is a $CH_2$ group.

Suitably, $R^{19}$ is attached meta to the —CHOH— moiety.

Preferably $R^{19}$ is a chlorine atom. A preferred group $R^{19}C_6H_4$— is the 3-chlorophenyl group.

Preferably $R^{20}$ is hydrogen.

Preferably $R^{21}$ is methyl.

Preferably m" is 1.

Certain compounds of the method of the invention (for example the compounds formula (I), wherein $R^4$ is other than a carboxylic acid salt, and the compounds of formula (II) which are esterified) may be provided as acid addition salts. Such salts may be of an organic or inorganic acid but are normally salts with a veterinarily acceptable acid. Suitable acid addition salts include those formed with acids such as hydrochloric, hydrobromic, orthophosphoric, sulphuric, methanesulphonic, toluenesulphonic, acetic, propionic, lactic, citric, fumaric, malic, succinic, salicylic, acetylsalicylic or the like acids.

A preferred acid addition salt of the compound of formula (I) is the fumarate salt, preferably the hemifumarate salt.

In addition to the above mentioned compounds, further suitable compounds of formula (I) or where appropriate, salts, esters or amides thereof, include those disclosed in EP0006735. Preferred compounds of formula (I), or where appropriate salts, esters or amides thereof, include those disclosed in EP0006735; it will be understood that the above mentioned suitable and preferred compounds of formula (I) include the suitable and preferred stereochemical isomers of the compounds of formula (I) disclosed in EP0006735.

In addition to the above mentioned compounds, further suitable compounds of formula (II) or where appropriate, salts, esters or amides thereof, include those disclosed in EP0023385. Preferred compounds of formula (II), or where appropriate salts, esters or amides thereof, include those disclosed in EP0023385; it will be understood that the above mentioned suitable and preferred compounds of formula (II) include the suitable and preferred stereochemical isomers of the compounds of formula (II) disclosed in EP0023385.

Suitable compounds of formula (III) or where appropriate, salts, esters or amides thereof, include those disclosed in EP0028105. Preferred compounds of formula (III), or where appropriate salts, esters or amides thereof, include those disclosed in EP0028105; it will be understood that the above mentioned suitable and preferred compounds of formula (III) include the suitable and preferred stereochemical isomers of the compounds of formula (III) disclosed in EP0028105.

Suitable compounds of formula (IV) or where appropriate, salts, esters or amides thereof, include those disclosed in EP0040915. Preferred compounds of formula (IV), or where appropriate salts, esters or amides thereof, include those disclosed in EP0040915; it will be understood that the above mentioned suitable and preferred compounds of formula (IV) include the suitable and preferred stereochemical isomers of the compounds of formula (IV) disclosed in EP0040915.

Suitable compounds of formula (V) or where appropriate, salts, esters or amides thereof, include those disclosed in EP0040000. Preferred compounds of formula (V), or where appropriate salts, esters or amides thereof, include those disclosed in EP0040000; it will be understood that the above mentioned suitable and preferred compounds of formula (V) include the suitable and preferred stereochemical isomers of the compounds of formula (V) disclosed in EP0040000.

Suitable compounds of formula (VI) or where appropriate, salts, esters or amides thereof, include those disclosed in EP0052963A. Preferred compounds of formula (VI), or where appropriate salts, esters or amides thereof, include those disclosed in EP0052963A; it will be understood that the above mentioned suitable and preferred compounds of formula (VI) include the suitable and preferred stereochemical isomers of the compounds of formula (VI) disclosed in EP0052963A.

Suitable compounds of formula (VII) or where appropriate, salts, esters or amides thereof, include those disclosed in EP0066351.

Preferred compounds of formula (VII), or where appropriate salts, esters or amides thereof, include those disclosed in EP0066351; it will be understood that the above mentioned suitable and preferred compounds of formula (VII) include the suitable and preferred stereochemical isomers of the compounds of formula (VII) disclosed in EP0066351.

Suitable compounds of formula (VIII) or where appropriate, salts, esters or amides thereof, include those disclosed in EP0061907. Preferred compounds of formula (VIII), or where appropriate salts, esters or amides thereof, include those disclosed in EP0061907; it will be understood that the above mentioned suitable and preferred compounds of formula (VIII) include the suitable and preferred stereochemical isomers of the compounds of formula (VIII) disclosed in EP0061907.

Suitable compounds of formula (IX) or where appropriate, salts, esters or amides thereof, include those disclosed in EP0070133A. Preferred compounds of formula (IX), or where appropriate salts, esters or amides thereof, include those disclosed in EP0070133A; it will be understood that the above mentioned suitable and preferred compounds of formula (IX) include the suitable and preferred stereochemical isomers of the compounds of formual (IX) disclosed in EP0070133A.

Suitable compounds of formula (X) or where appropriate, salts, esters or amides thereof, include those disclosed in EP0070134 and GB No. 1574208. Preferred compounds of formula (X), or where appropriate salts, esters or amides thereof, include those disclosed in EP0070134 and GB No. 1574208 it will be understood that the above mentioned suitable and preferred compounds of formula (X) include the suitable and preferred stereochemical isomers of the compounds of formula (X) disclosed in EP0070134 and GB No. 1574208.

Suitable compounds of formula (XI) or where appropriate, salts, esters or amides thereof, include those disclosed in EP0095827. Preferred compounds of formula (XI), or where appropriate salts, esters or amides thereof, include those disclosed in EP0095827; it will be understood that the above mentioned suitable and preferred compounds of formula (XI) include the suitable and preferred stereochemical isomers of the compounds of formula (XI) disclosed in EP0095827.

Suitable compounds of formula (XII) or where appropriate, salts, esters or amides thereof, include those disclosed in EP0099707. Preferred compounds of formula (XII), or where appropriate salts, esters or amides thereof, include those disclosed in EP0099707; it will be understood that the above mentioned suitable and preferred compounds of formula (XII) include the suitable and preferred stereochemical isomers of the compounds of formula (XII) disclosed in EP0099707.

Suitable compounds of formula (XIII) or where appropriate, salts, esters or amides thereof, include those disclosed in EP0139921A. Preferred compounds of formula (XIII), or where appropriate salts, esters or amides thereof, include those disclosed in EP0139921A; it will be understood that the above mentioned suitable and preferred compounds of formula (XIII) include the suitable and preferred stereochemical isomers of the compounds of formula (XIII) disclosed in EP0139921A.

Suitable compounds of formula (XIV) or where appropriate, salts, esters or amides thereof, include those disclosed in EP0142102A. Preferred compounds of formula (XIV), or where appropriate salts, esters or amides thereof, include those disclosed in EP0142102A; it will be understood that the above mentioned suitable and preferred compounds of formula (XIV) include the suitable and preferred stereochemical isomers of the compounds of formula (XIV) disclosed in EP0142102A.

Suitable compounds of formula (XV) or where appropriate, salts, esters or amides thereof, include those disclosed in EP0025331. Preferred compounds of formula (XV), or where appropriate salts, esters or amides thereof, include those disclosed in EP0025331; it will be understood that the above mentioned suitable and preferred compounds of formula (XV) include the suitable and preferred stereochemical isomers of the compounds of formula (XV) disclosed in EP0025331.

Suitable compounds of formula (XVI) or where appropriate, salts, esters or amides thereof, include those disclosed in EP0089154A. Preferred compounds of formula (XVI), or where appropriate salts, esters or amides thereof, include those disclosed in EP0089154A; it will be understood that the above mentioned suitable and preferred compounds of formula (XVI) include the suitable and preferred stereochemical isomers of the compounds of formula (XVI) disclosed in EP0089154A.

Suitable compounds of formula (XVII) or where appropriate, salts, esters or amides thereof, include those disclosed in EP0091749A.

Preferred compounds of formula (XVII), or where appropriate salts, esters or amides thereof, include those disclosed in EP0091749A; it will be understood that the above mentioned suitable and preferred compounds of formula (XVII) include the suitable and preferred stereochemical isomers of the compounds of formula (XVII) disclosed in EP0091749A.

Suitable compounds of formula (XVIII) or where appropriate, salts, esters or amides thereof, include those disclosed in EP0029320. Preferred compounds of formula (XVIII), or where appropriate salts, esters or amides thereof, include those disclosed in EP0029320; it will be understood that the above mentioned suitable and preferred compounds of formula (XVIII) include the suitable and preferred stereochemical isomers of the compounds of formula (XVIII) disclosed in EP0029320.

Suitable compounds of formula (XIX) or where appropriate, salts, esters or amides thereof, include those disclosed in EP0051917A. Preferred compounds of formula (XIX), or where appropriate salts, esters or amides thereof, include those disclosed in EP0051917A; it will be understood that the above mentioned suitable and preferred compounds of formula (XIX) include the suitable and preferred stereochemical isomers of the compounds of formula (XIX) disclosed in EP0051917A.

Suitable compounds of formula (XX) or where appropriate, salts, esters or amides thereof, include those disclosed in EP0140359A. Preferred compounds of formula (XX), or where appropriate salts, esters or amides thereof, include those disclosed in EP0140359A; it will be understood that the above mentioned suitable and preferred compounds of formula (XX) include the suitable and preferred stereochemical isomers of the compounds of formula (XX) disclosed in EP0140359A.

Suitable compounds of formula (XXI) or where appropriate, salts, esters or amides thereof, include those disclosed in EP0063004A. Preferred compounds of formula (XXI), or where appropriate salts, esters or amides thereof, include those disclosed in EP0063004A; it will be understood that the above mentioned suitable and preferred compounds of formula (XXI) include the suitable and preferred stereochemical isomers of the compounds of formula (XXI) disclosed in EP0063004A.

Suitable compounds of formula (XXII) or where appropriate, salts, esters or amides thereof, include those disclosed in EP170135A. Preferred compounds of formula (XXII), or where appropriate salts, esters or amides thereof, include those disclosed in EP170135A; it will be understood that the above mentioned suitable and preferred compounds of formula (XXII) include the suitable and preferred stereochemical isomers of the compounds of formula (XXII) disclosed in EP170135A.

Suitable compounds of formula (XXIII) or where appropriate, salts, esters or amides thereof, include those disclosed in EP0021636. Preferred compounds of formula (XXIII), or where appropriate salts, esters or amides thereof, include those disclosed in EP0021636; it will be understood that the above mentioned suitable and preferred compounds of formula (XXIII) include the suitable and preferred stereochemical isomers of the compounds of formula (XXIII) disclosed in EP0021636.

Suitable compounds of formula (XXIV) or where appropriate, salts, esters or amides thereof, include those disclosed in EP0102213A. Preferred compounds of formula (XXIV), or where appropriate salts, esters or amides thereof, include those disclosed in EP0102213A it will be understood that the above mentioned suitable and preferred compounds of formula (XXIV) include the suitable and preferred stereochemical isomers of the compounds of formula (XXIV) disclosed in EP0102213A.

The carbon atoms marked with a single asterisk "*" in compounds (I) and (II) are asymmetric carbon atoms.

In the compounds of formula (I) and (II) the carbon atoms marked with a double asterisk "**" are asymmetric carbon atoms, when $R^6 \neq R^7$ and $R^{4A} \neq R^{5A}$ respectively.

It will be clear from the above that the compounds of formula (I) or (II) may exist in at least two and often four stereoisomeric forms. The present invention encompasses the administration of all stereoisomers of the compounds of formula (I) whether free from other stereoisomers or admixed with other stereoisomers in any proportion and hence includes, for instance, racemic mixtures of enantiomers.

Suitably, in the compounds of formula (I), the "*" asymmetric carbon has the R-configuration.

Suitably, in the compounds of formula (II), the "*" asymmetric carbon has the R-configuration.

Suitably, in the compounds of formula (I), when $R^6 \neq R^7$, the "**" asymmetric carbon has the R-configuration.

Suitably, in the compounds of formula (II), when $R^{4A} \neq R^{5A}$, the "**" asymmetric carbon has the R-configuration.

Preferably, in the compounds of formula (I), when $R^6 \neq R^7$, a preferred enantiomer is that wherein: the "*"

asymmetric carbon=R-configuration; and the "*" asymmetric carbon=R-configuration; that is the RR enantiomer.

It will therefore be understood that a preferred diastereoisomer of the compounds of formula (I) is the RR:SS diastereoisomer.

Preferably, in the compounds of formula (II), when $R^{4A} \neq R^{5A}$, a preferred enantiomer is that wherein: the "*" asymmetric carbon=R-configuration; and the "**" asymmetric carbon=R-configuration, that is the RR enantiomer.

It will therefore be understood that a preferred diastereoisomer of the compounds of formula (II) is the RR:SS diastereoisomer.

Compounds of formula (I) or (II) having a single asymmetric carbon atom may, if desired, be separated into individual enantiomers by conventional means, for example by the use of an optically active acid as a resolving agent. Those compounds of formula (I) or (II) having two asymmetric carbon atoms may be separated into diastereoisomic pairs of enantiomers by, for example fractional crystallisation from a suitable solvent such as methanol or ethyl acetate or a mixture thereof. The pair of enantiomers thus obtained may be separated into individual stereoisomers by conventional means such as by the use of an optically active acid as a resolving agent.

Suitable optically active acids which may be used as resolving agents are described in "Topics in Stereochemistry" Vol 6, Wiley Interscience, 1971, Allinger, N. L. and Eliel, W. L. Eds.

Alternatively any enantiomer of a compound of formula (I) or (II) may be obtained by stereospecific synthesis using an optically pure starting material of known configuration.

Similarly, the present invention extends to administration of the individual steroisomeric forms of the compounds of formulae (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII) and (XXIV). The preferred sterochemical isomers of each of these compounds and the methods of obtaining them are as indicated above.

Preferably, the invention comprises the administration of a compound selected from the list consisting of:
N-[2-(4-carbomethoxyphenyl)-1-methylethyl]-2-hydroxy-2-(4-hydroxy-3-hydroxymethylphenyl)ethanamine;
N-[2-(4-carboxyphenyl)-1-methylethyl]-2-hydroxy-2-(4-hydroxy-3-hydroxymethylphenyl)ethanamine;
N-[2-(4-carboxyphenyl)-1-methylethyl]-2-hydroxy-2-phenylethanamine;
N-[2-(4-carbomethoxyphenyl)-1-methylethyl]-2-hydroxy-2-phenylethanamine;
N-[2-(4-carbomethoxyphenyl)-1-methylethyl]-2-hydroxy-2-(4-amino-3,5-dichlorophenyl)ethanamine;
N-[2-(4-carboxyphenyl)-1-methylethyl]-2-hydroxy-2-(4-amino-3,5-dichlorophenyl)ethanamine;
N-[2-(4-carbomethoxymethoxyphenyl)-1-methylethyl]-2-hydroxy-2-(4-amino-3,5-dichlorophenyl) ethanamine;
N-[2-(4-carboxymethoxyphenyl)-1-methylethyl]-2-hydroxy-2-(4-amino-3,5-dichlorophenyl) ethanamine;
N-[2-(4-carbomethoxymethoxyphenyl)-1-methylethyl]-2-hydroxy-2-(3-chlorophenyl) ethanamine; and
N-[2-(4-carboxymethoxyphenyl)-1-methylethyl]-2-hydroxy-2-(3-chlorophenyl) ethanamine; or a veterinarily acceptable acid addition salt thereof.

The compounds of formula (I), (IIIA) and (IVA) may suitably be prepared by conventional methods including those disclosed in EP 0,006,735.

The compounds of formula (IIA) and (VA) may suitably be prepared by conventional methods including those disclosed in EP 0,023,385.

Suitably, the compounds of formula (III), or where appropiate, salts, esters and amides thereof, are prepared by methods conventional in the art, for example those disclosed in EP0028105.

Suitably, the compounds of formula (IV), or where appropiate, salts, esters and amides thereof, are prepared by methods conventional in the art, for example those disclosed in EP0040915.

Suitably, the compounds of formula (V), or where appropiate, salts, esters and amides thereof, are prepared by methods conventional in the art, for example those disclosed in EP0040000.

Suitably, the compounds of formula (VI) or where appropiate, salts, esters and amides thereof, are prepared by methods conventional in the art, for example those disclosed in EP0052963A.

Suitably, the compounds of formula (VII) or where appropiate, salts, esters and amides thereof, are prepared by methods conventional in the art, for example those disclosed in EP0066351.

Suitably, the compounds of formula (VIII) or where appropiate, salts, esters and amides thereof, are prepared by methods conventional in the art, for example those disclosed in EP0061907.

Suitably, the compounds of formula (IX), or where appropiate, salts, esters and amides thereof, are prepared by methods conventional in the art, for example those disclosed in EP0070133A.

Suitably, the compounds of formula (X), or where appropiate, salts, esters and amides thereof, are prepared by methods conventional in the art, for example those disclosed in EP0070134 and GB1574208.

Suitably, the compounds of formula (XI), or where appropiate, salts, esters and amides thereof, are prepared by methods conventional in the art, for example those disclosed in EP0095827.

Suitably, the compounds of formula (XII), or where appropiate, salts, esters and amides thereof, are prepared by methods conventional in the art, for example those disclosed in EP0099707.

Suitably, the compounds of formula (XIII), or where appropiate, salts, esters and amides thereof, are prepared by methods conventional in the art, for example those disclosed in EP0139921.

Suitably, the compounds of formula (XIV), or where appropiate, salts, esters and amides thereof, are prepared by methods conventional in the art, for example those disclosed in EP0142102A.

Suitably, the compounds of formula (XV), or where appropriate, salts, esters and amides thereof, are prepared by methods conventional in the art, for example those disclosed in EP0025331.

Suitably, the compounds of formula (XVI) or where appropiate, salts, esters and amides thereof, are prepared by methods conventional in the art, for example those disclosed in EP0089154A.

Suitably, the compounds of formula (XVII), or where appropiate, salts, esters and amides thereof, are prepared by methods conventional in the art, for example those disclosed in EP0091749A.

Suitably, the compounds of formula (XVIII), or where appropiate, salts, esters and amides thereof, are prepared by methods conventional in the art, for example those disclosed in EP0029320.

Suitably, the compounds of formula (XIX) or where appropiate, salts, esters and amides thereof, are prepared by methods conventional in the art, for example those disclosed in EP0051917A.

Suitably, the compounds of formula (XX), or where appropiate, salts, esters and amides thereof, are prepared by methods conventional in the art, for example those disclosed in EP0140359A.

Suitably, the compounds of formula (XXI), or where appropiate, salts, esters and amides thereof, are prepared by methods conventional in the art, for example those disclosed in EP0063004A.

Suitably, the compounds of formula (XXII), or where appropiate, salts, esters and amides thereof, are prepared by methods conventional in the art, for example those disclosed in EP0170135A.

Suitably, the compounds of formula (XXIII), or where appropriate, salts, esters and amides thereof, are prepared by methods conventional in the art, for example those disclosed in EP0021636.

Suitably, the compounds of formula (XXIV) or where appropriate, salts, esters and amides thereof, are prepared by methods conventional in the art, for example those disclosed in EP0102213A. A compound of formulae (I), (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII) or (XXIV); or where appropriate, a veterinarily acceptable salt, ester or amide thereof("the compound"), will normally be administered orally, although non-oral modes of administration for example injection or implantation, are also envisaged.

The particular formulation used will depend upon the chosen mode of administration but in general will be that used conventionally in the mode of adminstration chosen.

In addition there is provided a veterinarily acceptable formulation, for increasing the weight gain and/or improving the feed utilisation efficiency and/or increasing the lean body mass and/or decreasing birth mortality rate and increasing post-natal survival rate of livestock which formulation comprises a compound selected from the list consisting of compounds of the hereinbefore defined, compounds of formulae: (I), (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII) and (XXIV); or, where appropriate, a veterinarily acceptable salt, ester or amide thereof; in combination with a veterinarily acceptable carrier therefor.

Suitably, the compounds are administered in the feedstuff or drinking water provided for the livestock. Conveniently the compounds are administered in feed-stuff or drinking water comprising from $10^{-3}$ ppm –500 ppm of the total daily feed or water intake, more usually 0.01 ppm to 250 ppm, suitably less than 100 ppm for example 0.1 to 10 ppm.

For administration in feed-stuff the compounds are conveniently formulated as a premix in association with a suitable carrier.

Accordingly, the present invention also provides a veterinarily acceptable premix formulation comprising a compound selected from the list consisting of compounds of the, hereinbefore defined, formulae: (I), (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII) and (XXIV); or, where appropriate, a veterinarily acceptable salt ester or amide thereof; in association with a veterinarily acceptable carrier therefor.

Suitable carriers are inert conventional agents such as powdered starch. Other conventional feed-stuff premix carriers may also be employed.

Suitably the premix formulation will contain from about 0.001% to about 95% by weight of the compound, more typically about 0.001% to about 20% by weight of the compound.

When the compounds are administered by non-oral mode for example injection or implantation, any conventional formulation may be used to administer the compounds; suitably, the invention comprises the administration of from about 0.1 μg/kg to about 50 mg/kg of the compounds, more usually about 1 μg/mg to about 25 mg/kg, preferably less than 10 mg/kg.

The formulations of the invention may be prepared by any conventional process; for example a premix formulation may conveniently be prepared by dissolving a compound in any suitable solvent; blending the resulting solution and carrier to the required proportions and removing the solvent by drying under appropriate conditions.

The present invention will now be illustrated with reference to the following Examples, which do not limit the scope of the invention in any way.

Preparations

The following compounds were prepared using methods disclosed in EP 0,006,735:

$P_1$—N-[2-(4-carbomethoxyphenyl)-1-methylethyl]-2-hydroxy-2-phenylethanamine; (Example 21 in EP 0,006,735).

$P_2$—N-[2-(4-carbomethoxyphenyl)-1-methylethyl]-2-hydroxy-2-(4-hydroxy-3-hydroxymethylphenyl) ethanamine; (Example 20 of EP 0,006,735 higher melting diastereoisomer).

$P_3$—1:1 mixture of diastereoisomers of $P_2$; (Example 1 in EP 0,006,735).

The following compounds were prepared using the methods disclosed in EP 0,023,385:

$P_4$—N-[2-(4-carbomethoxymethoxyphenyl)-1-methylethyl]-2-hydroxy-2-(3-chlorophenyl)ethanamine; (Example 6 in EP 0,023,385);

$P_5$—N-[2-(4-carbomethoxymethoxyphenyl)-1-methylethyl]-2-hydroxy-2-(4-amino-3,5-dichlorophenyl)ethanamine.

EXAMPLE 1

Female C57B1/6 genetically obese (ob/ob) or normal lean mice were fed on a powdered breeders diet and given the compounds either once daily by oral gavage, or by admixture with the diet for 28 days. Fifty parts per million (ppm) in the diet is equivalent to a dose level of about eight to ten (obese mice) or twelve to thirteen (normal mice) milligrams per kilogram body weight per day. Body lipid content and lean body mass were determined gravimetrically. There were seven or eight mice in each treatment group and results are expressed as a percentage of values for an untreated group of similar size.

| | Compound of | | Results % of control values | | | | |
|---|---|---|---|---|---|---|---|
| Type of mouse | Preparation No. | Dose | Food Intake | Weight Gain | Gain/ Intake | Lean Body mass | Amt. of Lipid |
| C57B1/6 | $P_1$ | 50 ppm | 119* | 200* | 168 | 111+ | 103 |
| (ob/ob) | $P_4$ | 0.46 ppm | 116+ | 143+ | 124 | 107* | 105 |
| | $P_2$ | 10 mg/kg po | 111 | 78 | 70 | 113* | 77+ |
| | $P_2$ | 36 ppm | 112* | 111 | 99 | 112+ | 101 |
| Lean | $P_3$ | 20 mg/kg po | 189α | 171 | 90 | 113* | 69* |
| | $P_2$ | 75 ppm | 107 | 128 | 120 | 107 | 78+ |
| | $P_5$ | 50 ppm | 108* | 125 | 116 | 108* | 65α |

Statistically significant effects of treatment: "*" means $P<0.05$, "+" means $P<0.01$ and "α" means $P<0.001$ (No statistical analysis of gain/intake has been performed).

EXAMPLE 2

Marshall sexed broiler chicken, 30 days old, were fed on a basal feed, which was designed as a practical broiler finisher feed. Additive (see below) was substituted for maize in this diet. The supplemented diets were fed until the birds were 56 days old.

| | Weight gain 30-56 days(g) | | Food conversion efficiency 30-56 days | |
|---|---|---|---|---|
| | Male | Female | Male | Female |
| Control | 1644 | 1309 | .367 | .329 |
| $P_1$(3 ppm) | 1784 | 1326 | .385 | .333 |

EXAMPLE 3

Female Sprague-Dawley rats were mated, fed on powdered rodent diet and given compound $P_1$ as a dietary admixture (150 ppm) from days 2-20 of gestation. Thereafter no further compound was given. Parturition occurred on day 22. The pups were weighed 24 hours after birth. 48 hours after birth 7 pups were removed at random from 3 control and 3 treated litters, placed at 29° C. and rectal temperature was monitored. Results are expressed as means of the number of values shown in parentheses±S.E.M.

| | Weight (g) | | Rectal temperature after 10 mins @ 29° C. | Drop in rectal temperature after 10 mins @ 29° C. |
|---|---|---|---|---|
| | All pups | Pups monitored for body temperature | | |
| Control | 5.3 ± 0.1 (78) | 5.0 ± 0.1 (7) | 29.4 ± 0.4 (7) | 2.76 ± 0.16 (7) |
| $P_1$(150 ppm) | 5.9 ± 0.1α (52) | 6.6 ± 0.4+ (7) | 31.2 ± 0.5+ (7) | 1.98 ± 0.06α (7) |

Statistically significant effects of treatment:
"+" means $P<0.01$ and "α" means $P<0.001$.

Statistically significant effects of treatment: "+" means $P<0.01$ and "α" means $P<0.001$.

Toxicology Data

No adverse toxicological effects were observed in any of the above experiments.

I claim:

1. A method for treating livestock to decrease birth mortality rate and increase post-natal survival rate, which method comprises the administration to the livestock of an effective, non-toxic amount of a compound of formula (I)

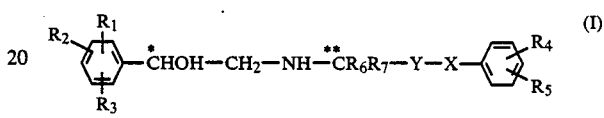

or a pharmaceutically acceptable salt thereof wherein $R^1$ is a hydrogen, fluorine or chlorine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino group; $R^2$ is a hydrogen, fluorine or chlorine atom or a hydroxyl group; $R^3$ is a hydrogen or chlorine atom or a hydroxyl group; $R^4$ is a carboxylic acid group or a salt, ester or amide thereof; $R^5$ is a hydrogen, chlorine or fluorine atom or a methyl, methoxyl or hydroxyl group or a carboxylic acid group or a salt, ester or amide thereof; $R^6$ is a hydrogen atom or a methyl, ethyl or propyl group; $R^7$ is a hydrogen atom or a methyl, ethyl or propyl group; X is an oxygen atom or a bond; and Y is an alkylene group of up to 6 carbon atoms or a bond; which compounds show anti-obesity and/or anti-hyperglycaemic activity or, where appropriate, a veterinarily acceptable salt, ester or amide thereof.

2. A method according to claim 1, wherein the administration to the livestock is carried out orally or non-orally.

3. A method according to claim 2, wherein the compound of formula (I) is a compound of formula:

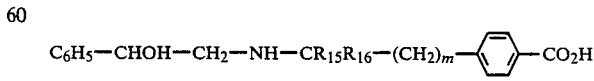

or a veterinarily acceptable salt, ester or amide thereof, wherein $R_{15}$ is hydrogen atom or a methyl group; $R_{16}$ is a hydrogen atom or a methyl group; and m is 1,2 or 3.

4. A method according to claim 2, wherein, the compound of formula (I) is a compound of formula:

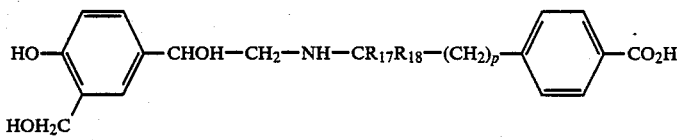

or a veterinarily acceptable salt, ester or amide thereof wherein $R_{17}$ is a hydrogen atom or a methyl group; $R_{18}$ is a hydrogen atom or a methyl group; and p is 1, 2 or 3.

5. A method according to claim 1, wherein the administration to the livestock is a compound selected from the group consisting of:
N-[2-(4-carbomethoxyphenyl)-1-methylethyl]-2-hydroxy-2-(4-hydroxy-3-hydroxymethylphenyl)ethanamine;
N-[2-(4-carboxyphenyl)-1-methylethyl]-2-hydroxy-2-(4-hydroxy-3-hydroxymethylphenyl)ethanamine;
N-[2-(4-carboxyphenyl)-1-methylethyl]-2-hydroxy-2-phenylethanamine;
N-[2-(4-carbomethoxyphenyl)-1-methylethyl]-2-hydroxy-2-phenylethanamine;
N-[2-(4-carbomethoxyphenyl)-1-methylethyl]-2-hydroxy-2-(4-amino-3,5-dichlorophenyl)ethanamine;
N-[2-(4-carboxyphenyl)-1-methylethyl]-2-hydroxy-2-(4-amino-3,5-dichlorophenyl)ethanamine;
N-[2-(4-carbomethoxymethoxyphenyl)-1-methylethyl]-2-hydroxy-2-(4-amino-3,5-dichlorophenyl)ethanamine;
N-[2-(4-carboxymethoxyphenyl)-1-methylethyl]-2-hydroxy-2-(4-amino-3,5-dichlorophenyl)ethanamine;
N-[2-(4-carbomethoxymethoxyphenyl)-1-methylethyl]-2-hydroxy-2-(3-chlorophenyl)ethanamine; and
N-[2-(4-carboxymethoxyphenyl)-1-methylethyl]-2-hydroxy-2-(3-chlorophenyl)ethanamine; or a veterinarily acceptable acid addition salt thereof.

6. A method according to claim 2, wherein the administration to the livestock is in the form of feedstuff or drinking water containing from $10^{-3}$ ppm to 500 ppm of compound or where appropriate a veterinarily acceptable salt, ester or amide thereof.

* * * * *